United States Patent [19]

Reiners et al.

[11] Patent Number: 4,868,325

[45] Date of Patent: Sep. 19, 1989

[54] (METH)-ACRYLIC ACID DERIVATIVES OF TRIISOCYANATES IN DENTISTRY

[75] Inventors: Jürgen Reiners, Leverkusen; Wolfgang Podszun, Cologne; Carlhans Süling, Odenthal; Jens Winkel, Cologne, all of Fed. Rep. of Germany

[73] Assignee: Bayer Aktiengesellschaft, Leverkusen, Fed. Rep. of Germany

[21] Appl. No.: 106,091

[22] Filed: Oct. 7, 1987

[30] Foreign Application Priority Data

Oct. 24, 1986 [DE] Fed. Rep. of Germany ....... 3636189

[51] Int. Cl.$^4$ ............................................. C07C 125/06
[52] U.S. Cl. ........................................ 560/115; 560/26
[58] Field of Search ........................ 560/26, 115, 158

[56] References Cited

U.S. PATENT DOCUMENTS

| 4,400,159 | 8/1983 | Orlowski et al. | 433/217.1 |
| 4,603,189 | 7/1986 | Knöfel et al. | 528/67 |
| 4,675,437 | 6/1987 | Knöfel et al. | 560/330 |
| 4,744,828 | 5/1988 | Winkel et al. | 106/35 |

FOREIGN PATENT DOCUMENTS 0173085 7/1985 European Pat. Off. .
2308036 10/1973 Fed. Rep. of Germany .

*Primary Examiner*—Joseph L. Schofer
*Assistant Examiner*—John J. Guarriello
*Attorney, Agent, or Firm*—Sprung Horn Kramer & Woods

[57] ABSTRACT

The new (meth)-acrylic acid derivatives of triisocyanates can be prepared by reacting appropriate triisocyanates with hydroxyalkyl (meth)-acrylates. The compounds can be employed as monomers for use in the dental field.

3 Claims, No Drawings

(METH)-ACRYLIC ACID DERIVATIVES OF TRIISOCYANATES IN DENTISTRY

The invention relates to new acrylic acid and methacrylic acid derivatives of triisocyanates, called (meth)-acrylic acid derivatives below, and to the preparation thereof. The new compounds can be employed as monomers for use in the dental field.

New (meth)-acrylic acid derivatives of triisocyanates, of the formula

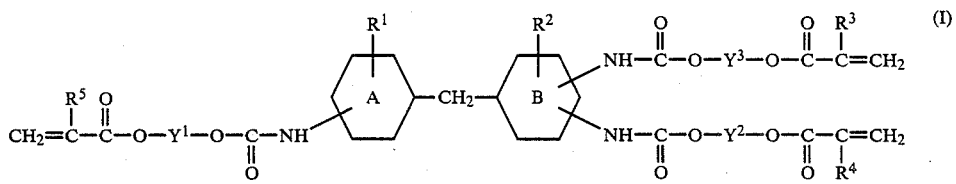

in which $R^1$ and $R^2$ are identical or different and represent hydrogen or a lower alkyl radical, $R^3$, $R^4$ and $R^5$ are identical or different and denote hydrogen or methyl, $Y^1$ to $Y^3$ are identical or different and denote divalent straight-chain or branched hydrocarbon radicals, having 2 to 15 carbon atoms, which may optionally contain 1 to 3 oxygen bridges and can optionally be substituted by 1 to 4 additional (meth)-acryloyloxy radicals, and the rings A and B are identical or different and can be aromatic or saturated, have been found. The (meth)-acrylic acid derivatives can exist as pure isomers or as a mixture of isomers. For the use according to the invention of the (meth)-acrylic acid derivatives in dental materials, it is particularly advantageous to employ the mixtures of isomers since they have a lower viscosity than the isomerically pure compounds.

In the context of the present invention, the substituents can, in general, have the following meaning:

Lower alkyl can denote a straight-chain or branched hydrocarbon radical having 1 to about 6 carbon atoms, preferably 1 to 4 carbon atoms. The following lower alkyl radicals may be mentioned as examples: methyl, ethyl, propyl, isopropyl, butyl, isobutyl, pentyl, isopentyl, hexyl and isohexyl.

Divalent hydrocarbon radicals $Y^1$ to $Y^3$ can denote straight-chain or branched aliphatic hydrocarbon radicals having 2 to 15 carbon atoms, preferably 2 to 10, carbon atoms. The radicals $Y^1$ and $Y^3$ can optionally contain 1 to 3 oxygen bridges, preferably 1 or 2 oxygen bridges. It is also possible for the radicals $Y^1$ to $Y^3$ to be substituted by 1 to 4, preferably 1 or 2, (meth)-acryloyloxy radicals. The following radicals may be mentioned as examples:

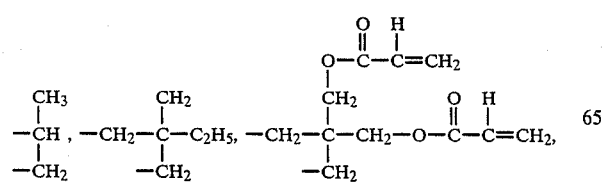

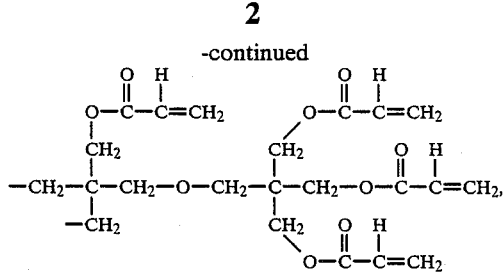

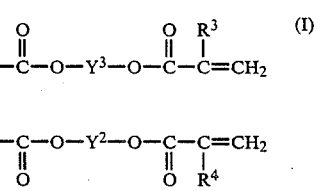

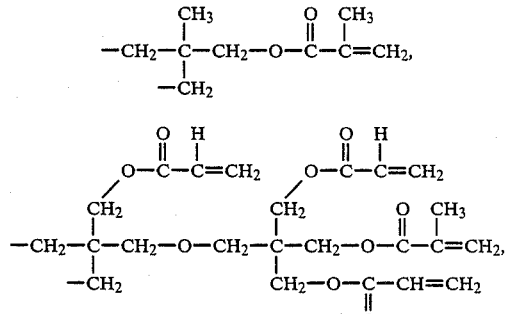

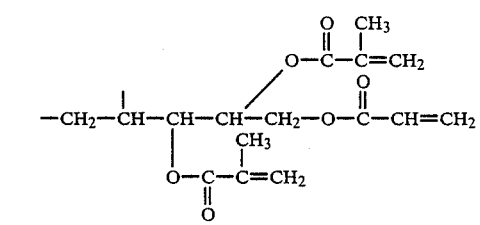

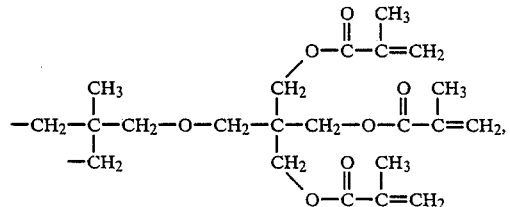

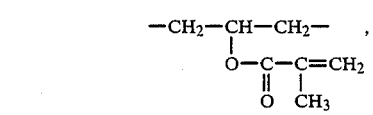

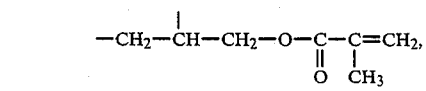

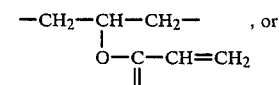

-continued

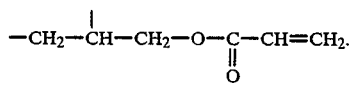

Ring A represents a benzene nucleus or a cyclohexane radical which contains two or three substituents. Ring B represents a benzene nucleus or a cyclohexane radical which contains three or four substituents.

The new (meth)-acrylic acid derivatives are colorless, non-volatile and, after polymerization, give transparent plastics having a high wear resistance.

They can be used particularly successfully in dental materials, such as dental filling materials and coating agents. The materials thus obtained are distinguished by a surprisingly high resistance against physical and chemical attack. The hardness and fracture resistance are improved to a particular extent compared to conventional materials which are employed for this purpose.

Preferred (meth)-acrylic acid derivatives are compounds of the formula

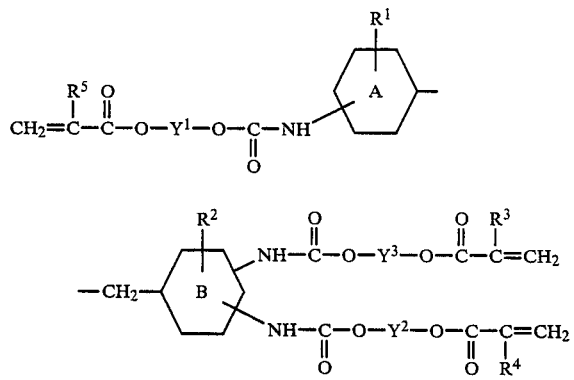

in which
  $R^1$ represents hydrogen,
  $R^2$ represents hydrogen or an alkyl radical having 1 to 4 carbon atoms,
  $R^3$, $R^4$ and $R^5$ are identical or different and denote hydrogen or methyl,
  $Y^1$ to $Y^3$ are identical or different and denote divalent straight-chain or branched aliphatic hydrocarbon radicals, having 2 to 10 carbon atoms, which may optionally contain 1 or 2 oxygen bridges and which can optionally be substituted by 1 or 2 additional (meth)-acryloyloxy radicals, ring B is aromatic or saturated, and ring A is saturated.

Particularly preferred (meth)-acrylic acid derivatives are those of the formula:

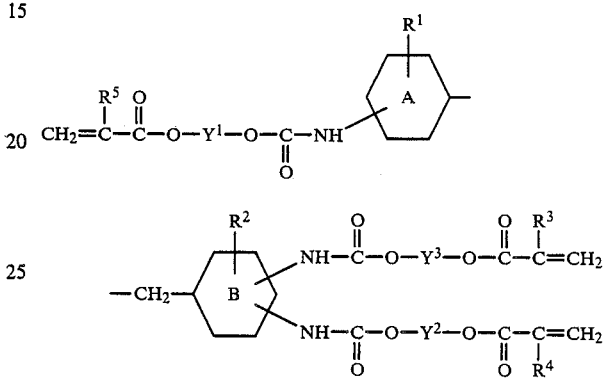

in which
  $R^1$ represents hydrogen,
  $R^2$ represents hydrogen or methyl,
  $R^3$, $R^4$ and $R^5$ are identical or different and denote hydrogen or methyl,
  $Y^1$ to $Y^3$ are identical or different and denote divalent straight-chain or branched aliphatic hydrocarbon radicals, having 2 to 10 carbon atoms, which may optionally contain 1 or 2 oxygen bridges and can optionally be substituted by 1 or 2 additional (meth)-acryloyloxy radicals, and
  rings A and B are saturated.

The following (meth)-acrylic acid derivatives may be mentioned as examples:

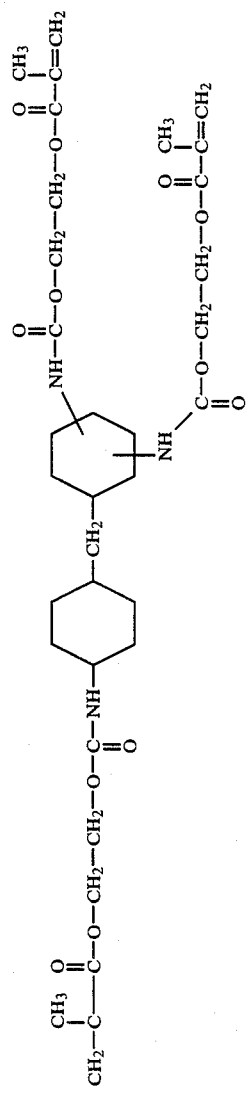
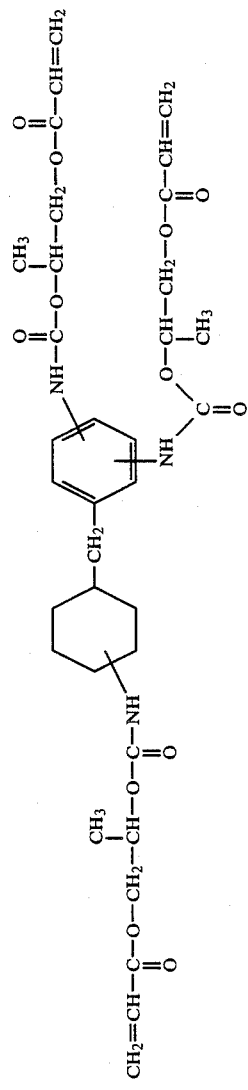
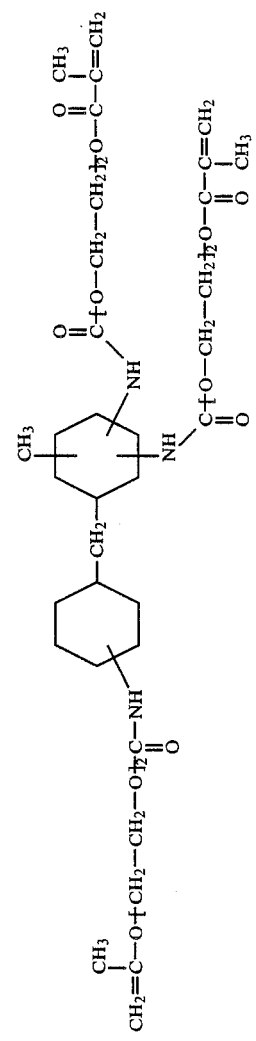

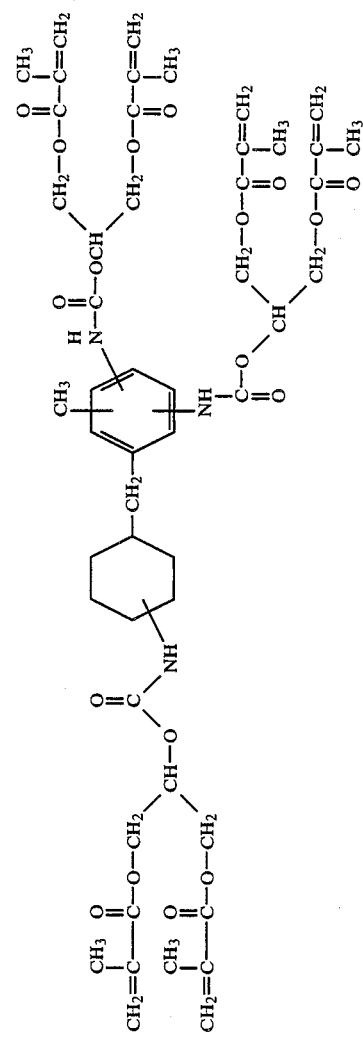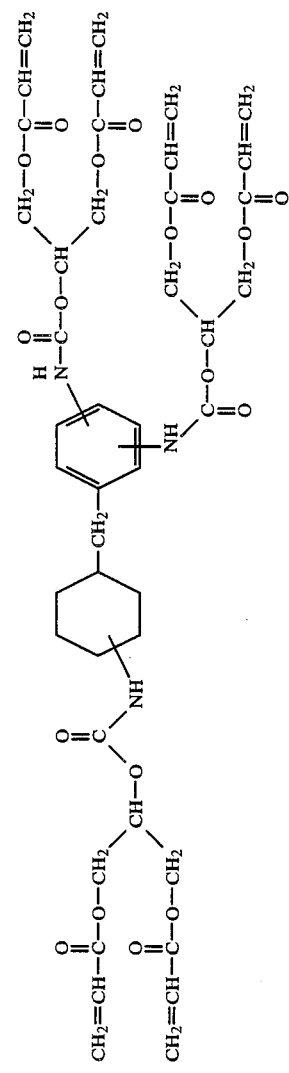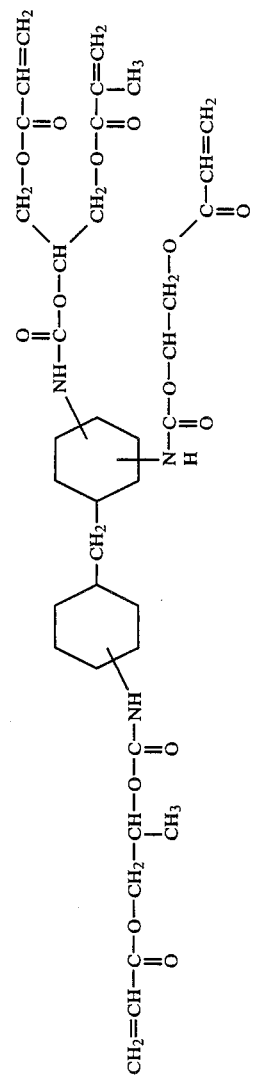

-continued
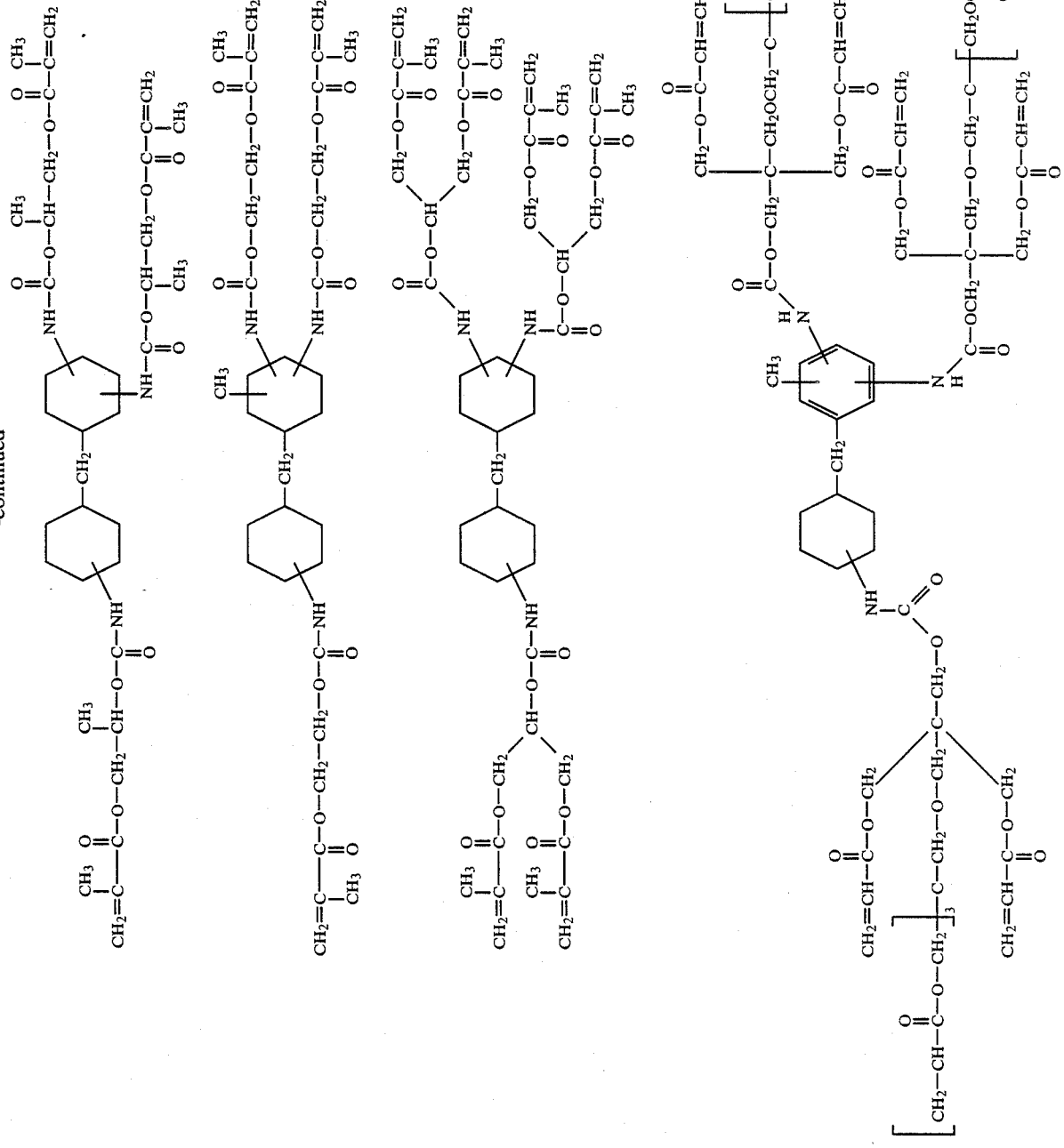

A process has also been found for the preparation of the (meth)-acrylic acid derivatives according to the invention which is characterized in that a triisocyanate of the formula

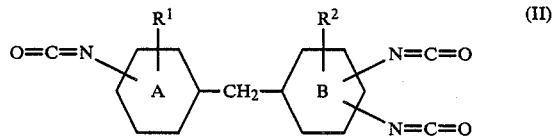 (II)

in which
R¹ and R² are identical or different and represent hydrogen or a lower alkyl radical, and rings
A and B are identical or different and can be aromatic or saturated, is reacted with a hydroxyalkyl (meth)-acrylate of the formula

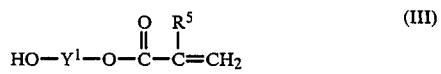 (III)

and/or

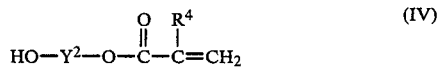 (IV)

and/or

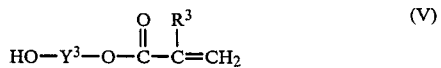 (V)

in which
$R^3$, $R^4$, $R^5$ and $R^6$ are identical or different and denote hydrogen or methyl, and
$Y^1$ to $Y^3$ are identical or different and denote divalent straight-chain or branced aliphatic hydrocarbon radicals, having 2 to 15 carbon atoms, which may optionally contain 1 to 3 oxygen
  bridges and can optionally be substituted by 1 to 4 additional (meth)-acryloyloxy radicals.

Triisocyanates of the formula II are known (DE-A1 3,417,684 and DE-A1 3,417,683) and can be obtained by phosgenation of appropriate triamino compounds.

Hydroxyalkyl (meth)-acrylates of the formula III to V are commercially available or can be prepared in a known fashion by partial esterification of appropriate polyols.

The process according to the invention is generally carried out in a manner such that, relative to each isocyanate group of the triisocyanate (II), 0.9 to 1.1, preferably 1.0 to 1.05 moles of a hydroxyalkyl (meth)acrylate of the formula III, IV or V , or mixtures of these compounds, are employed, where the sum of all hydroxyl equivalents, relative to each isocyanate group of the triisocyanate (II), must give 0.9 to 1.1, preferably 1.0 to 1.05.

The process according to the invention is generally carried out in an inert solvent with exclusion of water. Examples which may be mentioned are chloroform, tetrahydrofuran, acetone, dioxane, dichloromethane, toluene and acetonitrile. Preferred solvents are chloroform, toluene, acetone and dichloromethane.

The process according to the invention is generally carried out in a temperature range from 20 to 100° C., preferably from 30° to 70° C.

The process according to the invention is generally carried out at atmospheric pressure. However, it is also possible to carry out the process in the pressure range from 1 to 15 bar.

The reaction according to the invention for the preparation of urethane is preferably carried out with exclusion of water (preferably below 0.1% of water).

In order to accelerte the reaction, tin-containing catalysts, such as dibutyltin dilaurate, tin(II) octoate or dibutyltin dimethoxide, are preferably used.

It is also possible to employ compounds having tertiary amino groups, or titanium compounds as catalysts. The following catalysts may be mentioned as examples: diazabicyclo[2.2.2]octane, triethylamine, N-methylpiperidine, tetrabutoxy-titanium (Ullman, Encyclopadie der technischen Chemie [Encyclopaedia of Industrial Chemistry], Vol. 19, p. 306 (1981)).

In general, the catalyst is employed in an amount from 0.01 to 2.5% by weight, preferably from 0.1 to 1.5% by weight, relative to the total amount of reactants.

The reaction to form urethane is generally carried out in the presence of 0.01 to 0.2% by weight of a polymerization inhibitor, for example 2,6-di-tert.butyl-4-methylphenol.

The process according to the invention can be carried out as follows, for example:

The reactants are dissolved in the solvent, and the catalyst is added with stirring. The course of the reaction with time can be followed, for example, by measuring the IR spectra. After complete reaction of the isocyanate groups, the reaction products are isolated by removing the solvent. Prior purification with the aid of adsorbents, for example activated charcoal, bleaching earth, silica gel or aluminum oxide, is, of course, also possible.

The (meth)-acrylic acid derivatives of triisocyanates according to the invention can be used as monomers for the preparation of polymeric materials. The polymerization can be carried out, in a fashion known per se, by free-radical initiation, and produces polymers which have a high crosslinking density.

The (meth)-acrylic acid derivatives of triisocyanates according to the invention can be used, in particular, as monomers for dental materials. Dental materials which may be mentioned are, for example, filling materials for teeth, coating agents for teeth, and components for the production of tooth replacements. Depending on the area of application, dental materials may contain further auxiliaries.

For use as monomers for dental filling materials or coating agents (dental varnishes) in the dental field, the (meth)-acrylic acid derivatives of triisocyanates according to the invention can be mixed with comonomers which are known per se. Thus, for example, the viscosity can be matched to the application. These monomer mixtures generally have a viscosity in the range 60 to 10,000 mPa.s.

The following comonomers may be mentioned as examples: triethylene glycol dimethacrylate, tetraethylene glycol dimethacrylate, 1,12-dodecanediol dimethacrylate, 1,6hexanediol dimethacrylate, diethylene glycol dimethacrylate, 2,2-bis[p-(2'-hydroxy-3'methacryloyloxypropoxy)phenyl]propane and 2,2-bis[p-(2'-methacryloyloxethoxy)phenyl]propane. Also of advantage are comonomers having urethane groups, for example the known products of the reaction of 1 mol of a diisocyanate, for example hexamethylene diisocyanate, trimethylhexamethylene diisocyanate or isophorone diisocyanate, with 2 mols of a hydroxyalkyl (meth)acrylate, for example glycerol dimethacrylate, 2-hydroxypropyl acrylate, etc.

Further examples of comonomers are: trimethylolpropane tri(meth)-acrylate, bis-(meth)acryloyloxyethoxymethyl)tricyclo[5.2.1.0$^{2.6}$]decane (according to DE-A 2,931,925 and 2,931,926), 1,3-di((meth)acryloyloxypropyl)-1,1,3,3-tetramethyl-disiloxane and 1,3-bis(3(meth)acryloyloxyethylcarbamoyloxy-propyl)-1,1,3,3-tetramethyl-disiloxane. In particular, conomomers are preferred which have a boiling point above 100° C. at 13 mbar.

In the context of the present invention, it is likewise preferred that mixtures of different (meth)acrylic acid derivatives according to the invention be employed.

The proportion of (meth)-acrylic acid derivatives of triisocyanates according to the invention in the monomer mixtures is generally 10 to 90% by weight, preferably 20 to 75% by weight.

It is also possible to employ monomer mixtures which contain several comonomers.

The (meth)-acrylic acid derivatives of triisocyanates according to the invention, if appropriate as a mixture with the known monomers, can be cured to form crosslinked polymers using methods which are known per se (G.M. Brauer, H. Argentar, Am. Chem. Soc., Symp. Ser. 212, pp. 359–371 (1983). For so-called redox polymerization, a system comprising a peroxidic compound and a reducing agent, for example based on tertiary aromatic amines, is suitable. Examples of peroxides are: dibenzoyl peroxide, dilauroyl peroxide and di-4-chlorobenzoyl peroxide.

Tertiary aromatic amines which may be mentioned are, for example, N,N-dimethyl-p-toluidine, bis-(2-hydroxyethyl)-p-toluidine,bis-(2-hydroxyethyl)-3,5-dimethylaniline and N-methyl-N-(2-methyl-carbamoyloxypropyl)-3,5-dimethylaniline, described in DE-A 2,759,239.

The concentration of the peroxide or of the amine is advantageously selected so that it is 0.1 to 5% by weight, preferably 0.5 to 3% by weight, relative to the monomer mixture. The peroxide- and amine-containing monomer mixtures are stored separately until used.

Polymerization of the monomers according to the invention can also be induced by irradiation with UV light or visible light (for example in the wavelength range 230 to 650 nm). Suitable initiators for the photo-initiated polymerization are, for example, benzil, benzil dimethyl ketal, benzoin monoalkyl ether, benzophenone, p-methoxybenzophenone, fluorenone, thioxanthone, phenanthrenequinone and 2,3-bornandione (camphorquinone), if appropriate in the presence of synergistically acting photoactivators, such as N,N-dimethylaminoethyl methacrylate, triethanolamine or 4-N,N-dimethyl-aminobenzenesulphonic acid bisallylamide.

The execution of the photopolymerization process is described, for example, in DE-A 3,135,115.

Besides the initiators described above, light-screening agents and polymerization inhibitors which are known per se for this application can be added to the (meth)-acrylates according to the invention.

The light-screening agent and the polymerization inhibitor are each generally employed in an amount from 0.01 to 0.50 part by weight, relative to 100 parts by weight of the monomer mixture. The monomer mixtures can be employed, without addition of fillers, as coating agents for teeth (dental varnishes). After polymerization, a scratch-resistant coating on the substrate is obtained.

When used as dental filling materials, fillers are generally added to the monomer mixtures obtained. In order to be able to achieve a high filler content monomer mixtures which have a viscosity in the range 60 to 10,000 mPa.s are particularly advantageous. Inorganic fillers can advantageously be added to the monomer mixtures containing the compounds of the formula I according to the invention. Examples which may be mentioned are mountain crystal, quartzite, crystobalite, quartz glass, highly disperse silicic acid, aluminum oxide and glass ceramics, for example Lanthanum- and zirconium-containing glass ceramics (DE-A 2,347,591).

Inorganic fillers are preferably treated with an adhesion promoter in order to improve bonding to the polymer matrix of the polymethacrylate. The adhesion promotion can be achieved, for example, by treatment with organosilicon compounds (E.P. Pleuddemann, Progress in Organic coatings, 11, 297 to 308 (1983)). 3-Methacryloyloxypropyltrimethoxysilane is preferably employed.

The fillers for the dental filling materials according to the invention generally have an average particle diameter of 0.01 to 100 μm, preferably from 0.05 to 50 μm, particularly preferably 0.05 to 5 μm. It can also be advantageous to employ alongside one another several fillers which have different particle diameters and different degrees of silanization.

The proportion of filler in the dental filling materials is generally 5 to 85% by weight, preferably 50 to 80% by weight.

For the preparation of dental filling materials, the components are processed using commercially available compounders.

The proportion of the (meth)-acrylic acid derivatives according to the invention in the filling materials is generally 5 to 90% by weight, preferably 10 to 60% by weight, relative to the filling material. The curing of the dental filling materials to form a molded element ocurs in the tooth cavity using the abovementioned methods. As a consequence of the high wear resistance of the dental filling obtained, dental filling materials which contain the compounds according to the invention in polymerized form are particularly suitable for use in the posterior region.

The (meth)-acrylic acid derivatives of triisocyanates according to the invention can also be employed as components in the production of tooth replacements.

In this case, the monomers according to the invention are combined with the conventionally used components which are known per se. The monomers are preferably employed as a mixture with alkyl methacrylates, such as methyl methacrylate. In addition, bead polymers which are known per se can also be added. In order to adjust the tooth color known inorganic and organic color pigments and opacifiers can be added. The use of stabilizers and light-screening agents is also possible.

Plastic teeth are produced by free-radical polymerizatin of the dental materials with shaping. Processing is possible both by injection processes and compression processes and is generally carried out according to conventional production methods for teeth based on poly(methyl methacrylate), for example by thermal polymerization using polymerization initiators which are known per se, for example based on peroxides and azo compounds, such as dibenzoyl peroxide, dilauroyl peroxide, cyclophexyl percarbonate and azoisobutyrodinitrile. Mixtures of polymerization initiators having various decomposition temperatures are also highly suitable.

EXAMPLE 1

Preparation of the adduct of dicyclohexylmethane triisocyanate and glycerol dimethacrylate 45.45 g (0.15 mol) of dicyclohexylmethane triisocyanate (isomer mixture having an NCO content of 41.5% by weight) are dissolved in 100 ml of chloroform. 57 mg of 2,6-di-tert.-butyl-4-methyl-phenol and 100 mg of tin(II) octoate are added to this mixture. 102.6 g (0.45 mol) of glycerol dimethacrylate (isomer mixture of 1,3and 1,2-bis-methacryloyloxy-propanol) are added dropwise at 30° C. with stirring. When the addition is complete, the mixture is stirred at 50°–60° C. until the isocyanate groups have completely reacted.

The conversion is followed by measuring the IR spectra (isocyanate bands at $\sim 2200$ cm$^{-1}$).

The reaction mixture is cooled, stirred with activated charcoal, filtered through Celite ® and freed of solvent in a water-pump vacuum.

The residue is concentrated in a high vacuum to constant weight.

IR (film on KBr) [cm$^{-1}$]: $\nu$(N-H): 3400
(C=O): 1690–1750 (ester and amide I) $\nu$(C=O): 1000–1530
(amide II)
$\nu$(C=C): 1638 cm$^{-1}$.

EXAMPLE 2

The adduct of triisocyanato-dicyclohexylmethane and glycerol dimethacrylate is prepared as described in Example 1. When the reaction is complete, however, the reaction mixture is cooled, stirred with activated charcoal and filtered through Celite ®, and 95.95 g of triethylene glycol dimethacrylate are added. The mixture is concentrated in vacuo to constant weight. A color less monomer mixture, which can be employed directly as a monomer solution for the preparation of dental materials, is obtained. The content of (meth)-acrylic acid derivative according to the invention is 60.7% by weight.

EXAMPLE 3

Preparation of the adduct of triisocyanato-methyldicyclohexylmethane and glycerol dimethacrylate 38.9 g (0.1227 mole) of triisocyanato-methyldicyclohexylmethane (isomer mixture having an NCO content of 37% by weight0 are dissolved in 200 ml of chloroform, and 53.7 mg of 2,6-di-tert. butyl-4-methylphenol and 100 mg of dibutyltin dilaurate are added. 83.9 g (0.368 mol) of glycerol dimethacrylate (isomer mixture of 1,3and 1,2-bismethacryloyloxypropanol) are slowly added dropwise at 50° C. with stirring. The mixture is stirred at 50°–60° C. until complete conversion (IR check) of the isocyanate groups. The product is isolated as described in Example 1. The trisurethanehexamethacrylate obtained is no longer pourable at room temperature.

Dilution with triethylene glycol dimethacrylate to a content of 65% by weight of the (meth)-acrylic acid derivative according to the invention gives a usable monomer mixture having a viscosity of about 1 Pa.s.

EXAMPLE 4

Preparation of the adduct of triisocyanatodicyclohexylmethane with 2-hydroxypropyl acrylate 30.3 g (0.1 mol) of triisocyanato-dicyclohexylmethane (NCO content 41.5% by weight), 35 mg of 2,6-ditbutyl-4-methylphenol and 0.1 g of tin(II) octoate are dissolved in 100 ml of chloroform. 39 g (0.3 mol) of 2hydroxypropyl acrylate are added dropwise at room temperature. The mixture is stirred at 60° C. until complete conversion of the NCO groups. The reaction mixture is worked up analogously to Example 1. IR (film on KBr) [cm$^{-1}$]:
$\nu$(N-H): 3400, U (C=O): 1690–1760,
(C=O) (amide II): 1500, U (C=C): 1620, 1640

EXAMPLE 5

Preparation of the adduct of triisocyanato-dicyclohexylmethane and 2-hydroxypropyl methacrylate 30.3 g (0.1 mol) of triisocyanato-dicyclohexylmethane (NCO content 41.5% by weight), 37 mg of 2,6-ditert.-butyl-4-methylphenol and 0.1 g of tin-(II) octoate are reacted in 100 ml of chloroform at 60° C. with 43.2 g (0.3 mol) of 2-hydroxypropyl methacrylate. The product is isolated analogously to Example 1.

EXAMPLE 6

Production of a dental filling material 198.3 parts by weight of a monomer mixture from Example 2, comprising 60.7% by weight of the adduct of triisocyanato-dicyclohexylmethane and glycerol dimethacrylate and 39.3% by weight of triethylene glycol dimethacrylate, 0.4 part by weight of camphorquinone, 0.25 part by weight of benzil dimethyl ketal and 1.0 part by weight of 4-N,N-dimetylaminobenzene sulphonic acid bisallylamide are processed into a monomer solution under exclusion of light. This solution cures under the action of visible light and/or UV light at an exposure duration of 60 seconds to form a plastic which has a high mechanical stability.

For the preparation of a dental filling material, 38 parts by weight of the abovementioned monomer solution and 62 parts by weight of a pyrogenic silicic acid (Aerosil OX 50), silanized with 5% by weight of 3-methacryloyloxypropyl-trimethoxysilane, are processed at room temperature in a commercially available compounder to for a paste. A test element produced from this paste and cured using a commercially available dental lamp (Translux ®) according to DIN 13922, exhibits a very high modulus of flexion, very high flectional strength and improved abrasion resistance.

It is understood that the specification and examples are illustrative but not limitative of the present invention and that other embodiments within the spirit and scope of the invention will suggest themselves to those skilled in the art.

We claim:

1. A (meth)-acrylic acid derivative of a triisocyanate of the formula

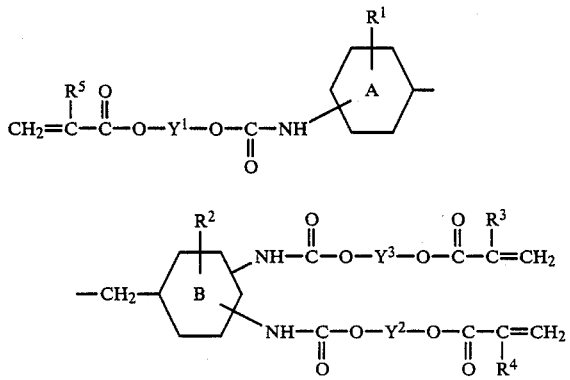

in which
- $R^1$ and $R^2$ are identical or different and represent hydrogen or a lower alkyl radical,
- $R^3$, $R^4$ and $R^5$ are identical or different and denote hydrogen or methyl,
- $Y^1$ to $Y^3$ are identical or different and denote divalent straight-chain or branched hydrocarbon radicals, having 2 to 15 carbon atoms, which may contain 1 to 3 oxygen bridges and can be substituted by 1 to 4 additional (meth)-acryloyl-oxy radicals, and the rings A and B are identical or different and can be aromatic or saturated.

2. A (meth)-acrylic acid derivative of a triiscocyanate according to claim 1, in which
- $R^1$ represents hydrogen,
- $R^2$ represents hydrogen or an alkyl radical having 1 to 4 carbon atoms,
- $R^3$ $R^4$ and $R^5$ are identical or different and denote hydrogen or methyl,
- $Y^1$ to $Y^3$ are identical or different and denote divalent straight-chain or branched aliphatic hydrocarbon radicals, having 2 to 10 carbon atoms, which may contain 1 or 2 oxygen bridges and which can be substituted by 1 or 2 additional (meth)-acryloyloxy radicals,
- ring B is aromatic or saturated, and
- ring A is saturated.

3. A (meth)-acrylic acid derivative of a triisocyanate according to claim 1, in which
- $R^1$ represents hydrogen,
- $R^2$ represents hydrogen or methyl,
- $R^3$, $R^4$ and $R^5$ are identical or different and denote hydrogen or methyl,
- $Y^1$ to $Y^3$ are identical or different and denote divalent straight-chain or branched aliphatic hydrogen radicals, having 2 to 10 carbon atoms, which may contain 1 or 2 oxygen bridges and can be substituted by 1 or 2 additional (meth)-acryloyloxy radicals, and
- rings A and B are saturated.

* * * * *